(12) United States Patent
Cho et al.

(10) Patent No.: US 8,101,473 B2
(45) Date of Patent: Jan. 24, 2012

(54) ROUNDED THREE-DIMENSIONAL GERMANIUM ACTIVE CHANNEL FOR TRANSISTORS AND SENSORS

(75) Inventors: Hans Cho, Palo Alto, CA (US); Theodore I Kamins, Palo Alto, CA (US); Nathaniel Quitoriano, Pacifica, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 207 days.

(21) Appl. No.: 12/501,259

(22) Filed: Jul. 10, 2009

(65) Prior Publication Data

US 2011/0006348 A1  Jan. 13, 2011

(51) Int. Cl.
*H01L 21/00* (2006.01)
*H01L 21/84* (2006.01)

(52) U.S. Cl. .. 438/164; 257/353; 257/347; 257/E27.112

(58) Field of Classification Search .................. 257/353, 257/347, E27.112; 438/164
See application file for complete search history.

(56) References Cited

U.S. PATENT DOCUMENTS

| | | | |
|---|---|---|---|
| 7,566,949 B2 * | 7/2009 | Dyer et al. | 257/628 |
| 7,906,814 B2 * | 3/2011 | Lee | 257/365 |
| 2007/0114610 A1 * | 5/2007 | Park | 257/353 |

OTHER PUBLICATIONS

Fang et al., "Vertically Stacked SiGe Nanowire Array Channel CMOS Transistors", IEEE Electron Device Letters, vol. 28, No. 3, Mar. 2007.
Yin et al., "Advanced Poly-Si TFT with Fin-Like Channels by ELA", IEEE Electron Device Letters, vol. 27, No. 5, May 2006.
Qi et al., "SiGe Nanowire Field Effect Transistors", Journal of Nanoscience and Nanotechnology, 2008, vol. 8, No. 1, pp. 457-460.
Jeong et al., "Mobility and Effective Electric Field in Nonplanar Channel MOSFETs", IEEE Transactions on Nanotechnology, vol. 8, No. 1, Jan. 2009.

* cited by examiner

*Primary Examiner* — Phat Cao
(74) *Attorney, Agent, or Firm* — David W. Collins

(57) ABSTRACT

A process is provided for fabricating rounded three-dimensional germanium active channels for transistors and sensors. For forming sensors, the process comprises providing a crystalline silicon substrate; depositing an oxide mask on the crystalline silicon substrate; patterning the oxide mask with trenches to expose linear regions of the silicon substrate; epitaxially grow germanium selectively in the trenches, seeded from the silicon wafer; optionally etching the $SiO_2$ mask partially, so that the cross section resembles a trapezoid on a stem; and annealing at an elevated temperature. The annealing process forms the rounded channel. For forming transistors, the process further comprises depositing and patterning a gate oxide and gate electrode onto this structure to form the gate stack of a MOSFET device; and after patterning the gate, implanting dopants into the source and drain located on the parts of the germanium cylinder on either side of the gate line.

14 Claims, 11 Drawing Sheets

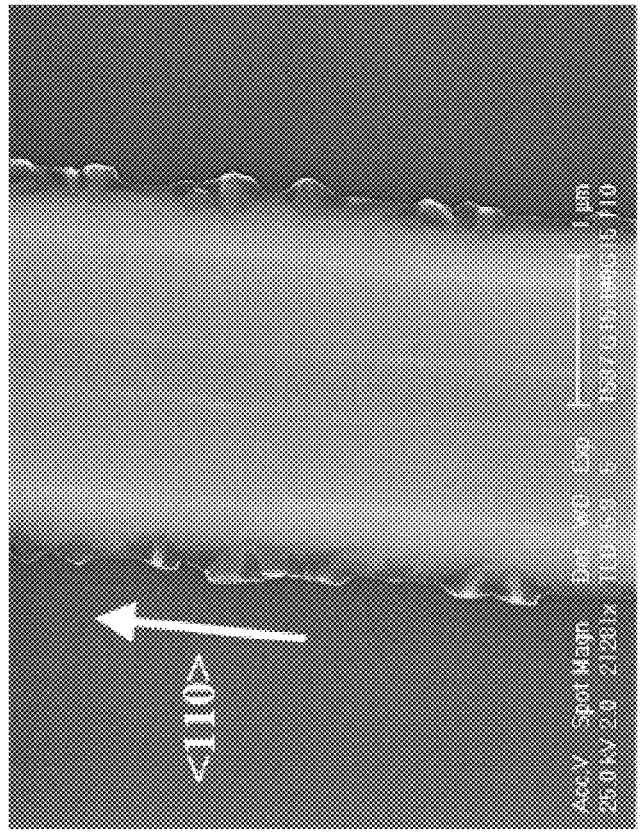
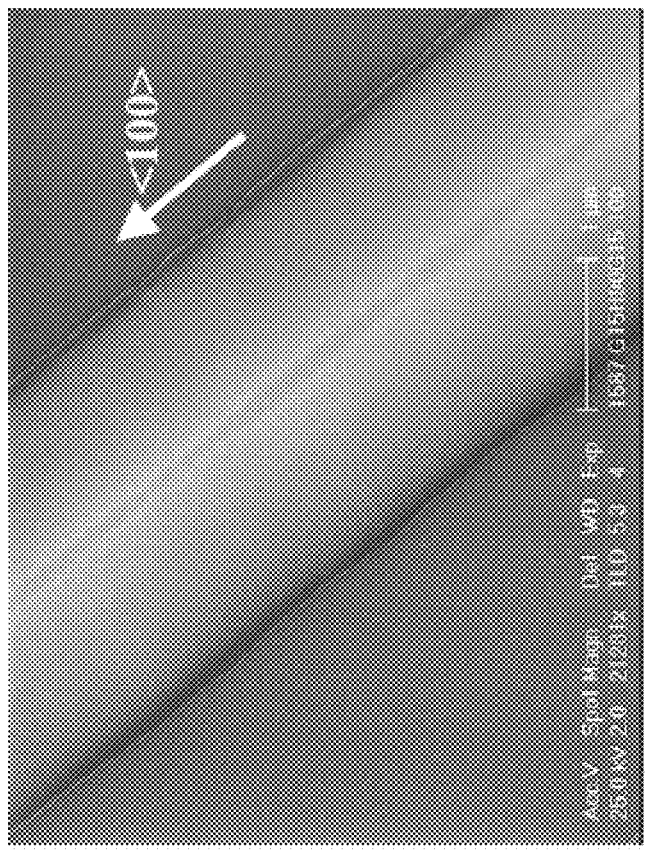
Fig. 6B
Fig. 6A

ROUNDED THREE-DIMENSIONAL GERMANIUM ACTIVE CHANNEL FOR TRANSISTORS AND SENSORS

BACKGROUND ART

Silicon as a device platform is nearing a fundamental limitation to further advances in device miniaturization. Key issues that motivate a new material and device structure include silicon's limited carrier mobility and limits to gate control over the MOSFET (metal-oxide-semiconductor field effect transistor) channel (as measured by metrics such as subthreshold swing and leakage current) as gate lengths and gate oxide thicknesses decrease according to Moore's law.

Germanium (Ge) is an ideal material for electronic devices due to its higher carrier mobility compared to those of silicon (Si), and is also considered to be relatively compatible with modern Si CMOS processing. However, because of its 4% lattice mis-match with Si, Ge grown directly onto Si contains crystal defects, such as dislocations, which are detrimental to device performance. In addition to crystal defects, surface roughness is also an artifact of heteroepitaxy that can degrade optical device performance by causing scattering loss. Therefore, the application of Ge films and structures integrated onto Si-based chips will depend on successfully growing smooth, low defect-density Ge films directly onto Si substrates.

Two methods previously used to eliminate defects are cyclical hydrogen annealing and defect-necking. Cyclical hydrogen annealing involves growing a film of Ge on Si, then annealing it in an $H_2$ ambient to cause the defects to concentrate at the Si/Ge interface, followed by additional Ge epitaxy. Defect-necking involves selectively growing Ge through an aperture etched through a $SiO_2$ mask so that the defects are intercepted and terminated at the aperture walls.

Two specific devices of interest are MOSFETs and field-effect sensors (FESs).

In order to enhance the performance of MOSFET devices, the area of the channel covered by the gate relative to the channel's effective cross-section (the area through which the source-drain current flows) has been increased by shaping the channel region into three-dimensional shapes such as fins (FinFETs), beams, and wires, and covering them on two, three, or four sides by the gate electrode, thereby increasing the gate's control over the channel. However, these device structures are obtained by etching, which causes surface roughness and damage that deleteriously affects device performance. In addition, these lithographically patterned structures contain acute angles at which electrical fields can be concentrated. Removing this roughness requires oxidation and removal of the surface and/or a high temperature anneal that smoothes the surface and acute angles. For silicon, this anneal requires temperatures in excess of 1000° C., which possibly jeopardizes the microstructural integrity of the wafer and/or any devices previously fabricated thereon.

Germanium-based devices have been developed, but these are mostly planar devices, and do not incorporate annealing for adjusting the shape.

Field-effect sensors have been developed with planar and nanowire channels. As the sensors' sensitivity increases with the relative area of the channel surface that is in contact with the sensed medium, planar structures are at a disadvantage. Nanowire channels have the requisite form factor, but growing them in a controllable, massively integratable manner is highly difficult.

BRIEF DESCRIPTION OF THE DRAWINGS

The various features of embodiments of the present invention may be more readily understood with reference to the following detailed description taken in conjunction with the accompanying drawings, where like reference numerals designate like structural elements, and in which:

FIGS. 6A-6B are each plan-view SEM images of Ge selectively grown for 15 minutes, followed by a 90 minute anneal in $H_2$ at 850° C., and further growth of Ge for 15 minutes, which are line oriented in the <110> direction (FIG. 6A) and line oriented in the <100> direction (FIG. 6B), in accordance with an embodiment of the invention.

DETAILED DESCRIPTION OF THE EMBODIMENTS

Figure 1:
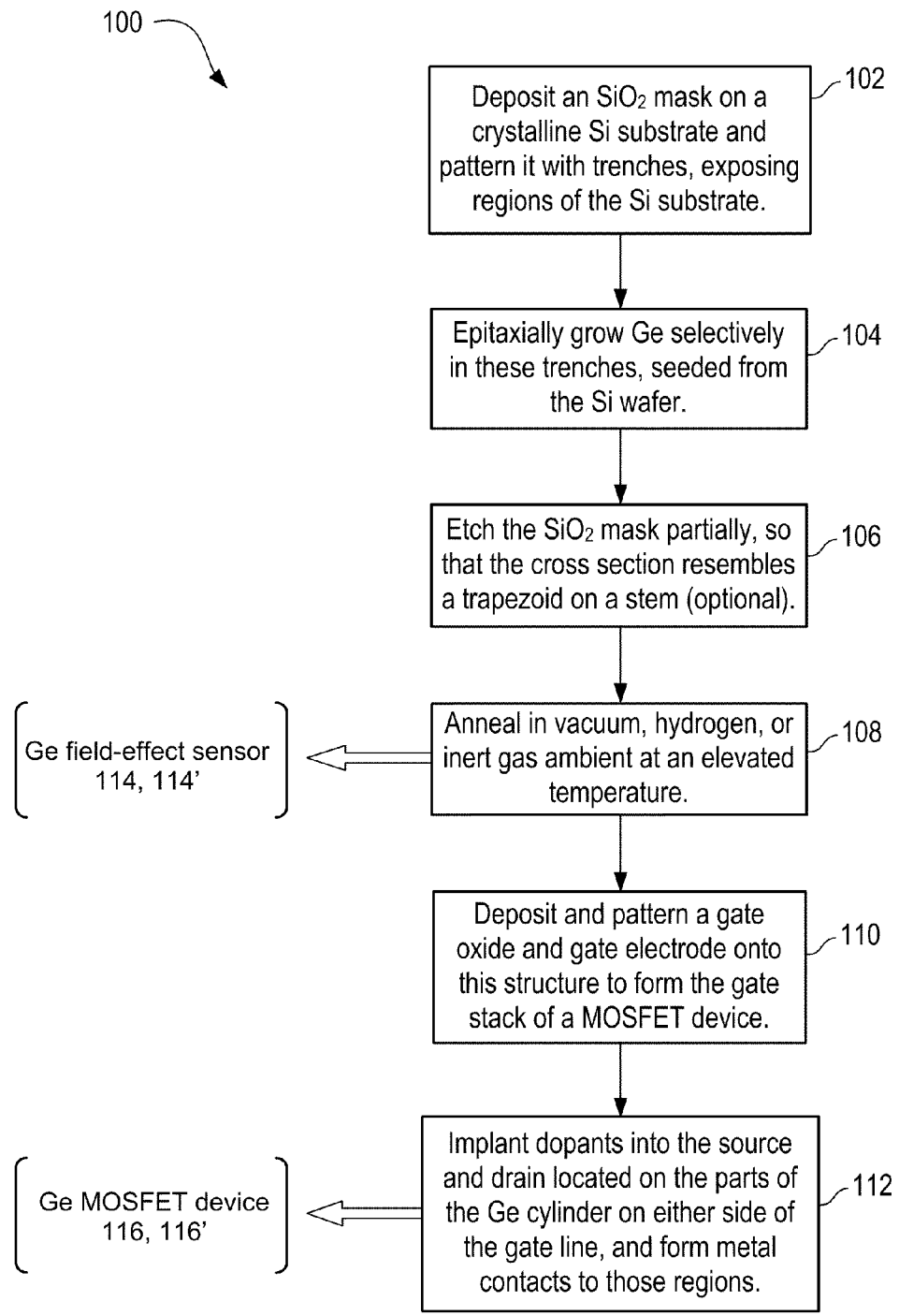
FIG. 1 is a flow diagram of a process in accordance with an embodiment of the invention.

Silicon as a device platform is nearing a fundamental limitation to further advances in device miniaturization. Key issues that motivate a new material and device structure include silicon's limited carrier mobility and limits to gate control over the MOSFET channel (as measured by metrics such as subthreshold swing and leakage current) as gate lengths and gate oxide thicknesses decrease according to Moore's law.

A material with a higher carrier mobility, such as germanium, can extend the lifetime of CMOS-based computing technologies by replacing silicon in some key applications. However, methods of incorporating Ge have focused on planar device structures where Ge is epitaxially grown onto a flat Si surface and used in the same way as conventional Si devices.

Three-dimensional channel structures with a gate covering more than two sides of the channel, such as FinFETs and Omega-FETs, have been developed for Si-based devices to increase control of the gate over the channel, but require high-temperature annealing to remove roughness and damage induced by the etching involved in the formation of such structures. The acute angles present in lithographically patterned three-dimensional channel structures also are the source of "hot spots" of high gate field concentration, and present a problem for device reliability.

In another realm of application, highly sensitive sub-micron scale field-effect sensors (FES) for light, chemicals, and biological agents are in increasing demand. The performance criteria for such sensors closely follow those of MOSFET devices, and therefore the problems stated above are relevant to field effect sensors as well. The sensitivity of a FES will increase if the channel is in the nanoscale and if the area of the channel surface in contact with the sensed medium is relatively large.

Germanium is a strong candidate for a replacement material for silicon in the semiconductor industry, and devices such as transistors utilizing Ge in their active regions promise significant performance enhancements due to the higher carrier mobility of Ge. Embodiments of the present invention are directed to a novel device structure achieved by annealing an epitaxially grown Ge channel into a semi-cylindrical or cylindrical shape, also referred to herein as a round or rounded shape. Further, a MOSFET device and a family of sensor devices utilizing this channel as the active region are provided.

In accordance with embodiments disclosed herein, a method of growing Ge is provided for forming morphologically smooth Ge regions; these regions are expected to be sufficiently defect-free to allow satisfactory device performance.

Germanium, in addition to being desirable for its electronic transport properties, can be grown and processed at much lower temperatures than Si. In particular, three-dimensional Ge structures appreciably deform and become rounded at temperatures as low as 700° C. Using this property, smooth, rounded Ge channels can be fabricated by the following process 100, with reference to FIG. 1:

On a crystalline Si substrate, deposit an $SiO_2$ mask and pattern it with trenches, exposing regions of the Si substrate (Step 102). The trenches may be of high aspect ratio in some embodiments. Further, the cross-sectional shape of the trench (defined as a long, relatively deep trough with steep or vertical sides) may not only be rectangular (as shown, for example, in FIGS. 2A-2I) but also may be square, polygon, curved, or other shapes. The trench may be linear on the plane of the substrate (as shown, for example, in FIGS. 3A-3D) but also may be curved, combinations of multiple such trenches, dots (to form hemispheres), closed line shapes such as circles and polygons (not filled), etc. The term "trench" is intended to include all such shapes and configurations.

Epitaxially grow Ge selectively in these trenches, seeded from the exposed Si regions of the wafer (Step 104). Grow Ge until it overgrows the mouth and edges of the trenches and begins to protrude outwards. At this stage, the epitaxial Ge body outside of the trench mouth will have a trapezoidal cross section. The epitaxial defects associated with the crystal lattice mismatch between Si and Ge will be largely confined to the interface region, away from the top of the trench, where the device will eventually be located.

Etch the $SiO_2$ mask partially, so that the cross section resembles a trapezoid on a stem or narrower pedestal (Step 106). In some embodiments, this step may be skipped.

Anneal in vacuum, hydrogen, or inert gas ambient at an elevated temperature (Step 108). The elevated temperature may be in the range of about 700° to 900° C. The Ge body above the plane of the $SiO_2$ surface will deform and assume an energetically more stable rounded state via heat activated surface diffusion of Ge atoms. The final shape of the cross section is determined by the initial shape and the extent of the anneal in terms of thermal budget (temperature and time), and will mostly resemble in cross-section a semi-oval or semi-circle attached to the Ge region lying below the plane of the $SiO_2$ surface. If the initial trench was linear, the overall shape of the Ge channel will be a semi-cylinder. (Note: Although its surface is smooth, it will contain low-angle crystallographic facets.) In cross-section, such a rounded structure may be somewhat more or less than half a circle, such as shown in FIG. 2F below, called "vaulted" herein. Or, the rounded structure may be considerably more than half a circle, forming an omega-shape, as shown in FIG. 2I below. Indeed, the cross-sectional shape may be mostly rounded, with a flat region at the bottom.

At this stage, if the Ge channel as formed in Step 108 above is very narrow, then the Ge channel can be used as an active region of a field-effect sensor 114, 114', as the current passing through the channel under a voltage bias from one end to the other will be affected by the presence of molecules or species attached to its surface.

For depletion-mode devices: The channel radius is comparable to or less than the extrinsic Debye length, which depends on the dopant concentration in the channel. For example, for doping of $2 \times 10^{18}$ cm$^{-3}$, the channel diameter would be about 100 nm.

However, other cases work also. The channel may be doped so that there is no conducting channel initially, and then a conducting channel is induced near the surface to connect the source and drain. This method applies to an accumulation-mode or inversion-mode device and is more applicable to a transistor than to a sensor, especially when used as a switching device, rather than as an analog device.

If the sensor is contemplated for use as a depletion-mode or accumulation-mode device, the trench should be narrow enough that the stem filling the trench is fully depleted to electrically isolate the channel from the substrate. For use as an inversion-mode device, the isolation is provided automatically (unless Ge in the trench also inverts because of surface charge).

In any event, a sensor device may be formed by attaching electrodes to either end of the semi-cylindrical, or rounded, channel, forming an insulator, such as an oxide, along a region of the channel along the surface in between the electrodes, and appropriately functionalizing a segment of that region with a receptor species or nanostructure that will specifically bind to a target molecule or species and/or be altered in its electronic state by the target species in a manner that interacts with and affects the electronic carriers within the Ge channel. In some cases, the channel surface is passivated with a conformal deposited or grown insulator (e.g., oxide or nitride) layer or multiple conformal layers, and a window is patterned to expose a portion of the channel surface or an insulator layer thereon for functionalization. In some cases, functionalization may be performed by using a resist (photo, contact imprint, or electron-beam) mask to define an opening corresponding to the area to be functionalized. One or more of the deposited dielectric layers may be etched away to expose the desired layer (either an underlying dielectric or the germanium channel surface). The functionalizing agent can be deposited uniformly over all exposed surfaces, after which the resist and the functionalizing agent deposited onto the resist are removed, leaving the functionalizing agent only in the defined opening.

In another method of fabrication, after an opening is optionally defined in a dielectric layer, an electric current may be flowed through the Ge channel while the entire structure is submersed in a solution containing the functionalizing agent or its precursors, such that the heat generated at the opening promotes selective deposition of the functionalizing agent on the Ge or an insulator surface exposed at the opening. In some cases, functionalization is not necessary, as the Ge surface or the insulator on it may directly interact with the target species. Field-effect sensors are described in greater detail below, with reference to FIGS. 2A-2F, 3A, and 3C.

To complete the field-effect sensor, dopants are implanted into the source and drain located on the parts of the Ge cylinder on either end of the channel, and metal contacts are formed to those regions. Alternately, metal-semiconductor Schottky junctions may be formed at the source and drain regions.

Continuing on with the description of FIG. 1, a MOSFET device may be formed by the following steps after the anneal (Step 108):

Deposit and pattern a gate insulator (e.g., an oxide) and gate electrode onto this structure to form the gate stack of a MOSFET device (Step 110). In some embodiments, a gate oxide can be formed by growing a thin layer of Si or SiGe selectively onto the channel surface and oxidizing it. In some embodiments, the thin layer of Si or SiGe is epitaxially grown onto the channel surface. In other embodiments, the deposited layer is not single crystal, as long as it is fully oxidized (or epitaxially regrows during the oxidation process).

After patterning the gate, implant dopants into the source and drain located on the parts of the Ge cylinder on either side of the gate line, and form metal contacts to those regions (Step 112). Alternately, metal-semiconductor Schottky junctions can be formed at the source and drain regions. The channel, gate stack, and source and drain regions together define a Ge MOSFET device 116, 116'.

Relative to previous MOSFETs (Si-based and planar Ge-based), the rounded channel structure and the enhanced carrier mobility are a combination brought about by utilizing the unique properties of Ge (low melting/epitaxy/processing temperatures and high electron and hole mobility). Because of the smooth, rounded channel, scattering of charge carriers at the rough surface and other damage-induced defect states is eliminated. The three-dimensional cylindrical shape with conforming gate ensures good electrostatic control of the channel, enabling strong control over the channel ON-OFF states. All this can be achieved at much lower processing temperatures than for a similar structure composed of Si, with a much higher gain in performance due to the transport properties of Ge. MOSFETS are described in greater detail below, with reference to FIGS. 2A-2B, 2G-2I, 3B, and 3D.

Relative to most catalyzed nanowire-based field-effect sensors, control over the location of the channels is lithographically achieved. Without subscribing to any particular theory, it is thought that the surface atoms of selectively grown Ge lines rearrange to minimize the total surface energy during annealing at, for example, 850° C. in a $H_2$ ambient. The increased temperature, which is near the melting temperature of Ge (937.4° C.), and the presence of $H_2$ enhance the rate of this morphological change by allowing increased surface diffusion of Ge atoms, enabling them to redistribute to the more energetically favorable configuration. When growth is resumed after this step, roughness begins to develop again in the <110> oriented lines, but not in the <100> oriented lines. While $H_2$ is useful in some embodiments, it is desirable to eliminate oxide-forming species that will limit surface migration of Ge atoms. Hydrogen is good because it can reduce traces of oxide (or prevent them from forming). In the absence of oxygen, water, or other oxide-forming species, vacuum (e.g., ultra high vacuum) or a very pure inert atmosphere work well also. The practical aspects of obtaining the pure environment will guide one's decision on the ambient atmosphere.

It is important to note that hydrogen anneal methods were developed to reduce growth defects from the majority of a continuous planar film of epitaxial Ge. It is expected that the growth defects have been reduced in the <100> oriented selectively grown Ge lines as well. The elimination of the surface roughness in a three-dimensional structure of epitaxial Ge by hydrogen annealing, and the sustained smoothness in growth morphology after the annealing step, is an additional benefit that can be exploited in the fabrication of loss-sensitive, three-dimensional optoelectronic structures and devices such as photodetectors or modulators integrated with optical waveguides.

Figure 2A:
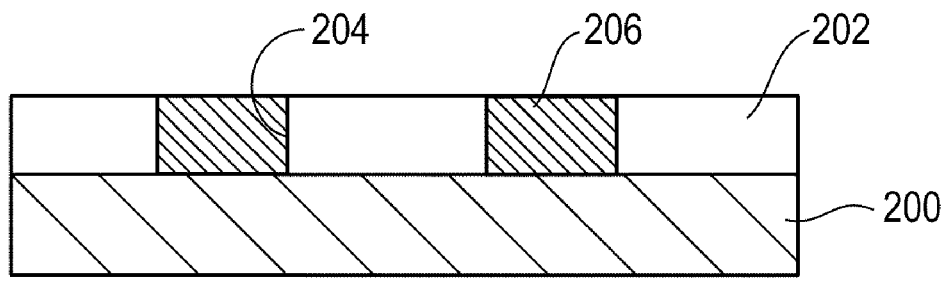
FIGS. 2A-2I are cross-sectional views, depicting different embodiments of the process sequence, wherein FIGS. 2A-2F result in vaulted three-dimensional channels and FIGS. 2A-2B and 2G-2I result in omega-shaped three-dimensional channels.
Figure 2B:
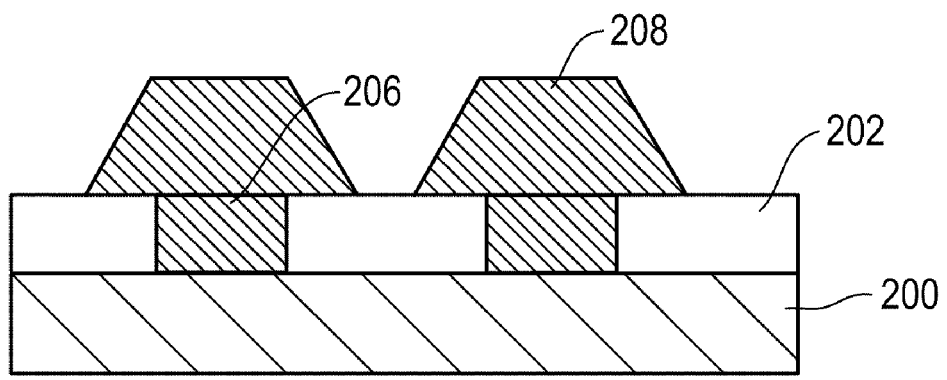
Figure 2C:
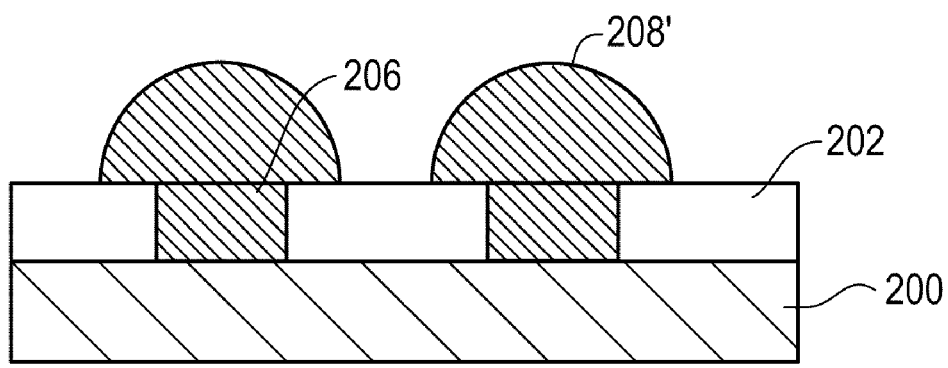
Figure 2D:
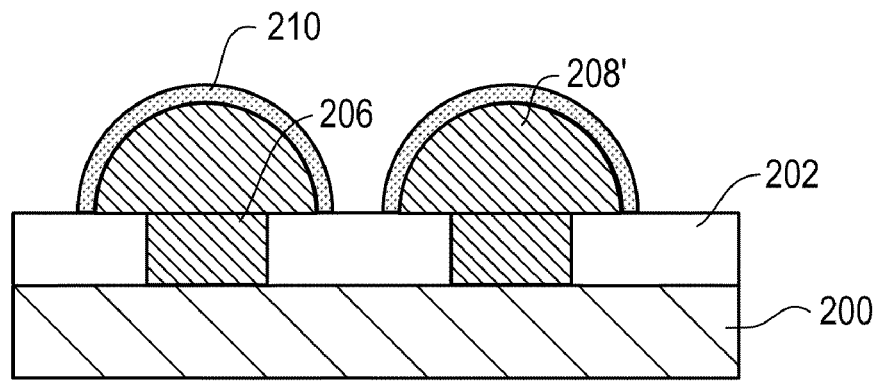
Figure 2E:
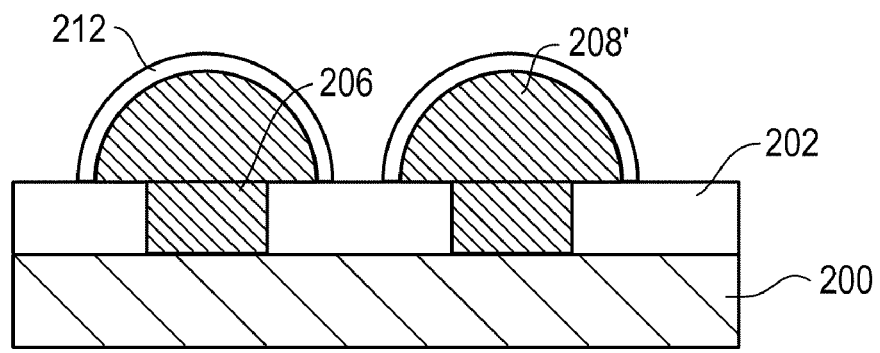
Figure 2F:
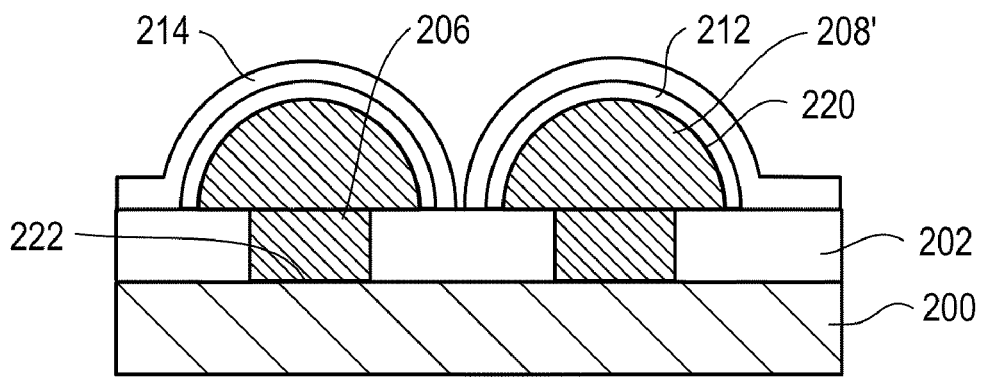

FIGS. 2A-2F depict a first embodiment for forming vaulted three-dimensional channels, useful in field-effect sensors (FIGS. 2A-2C) or in MOSFETs (FIGS. 2A-2F). As shown in FIG. 2A, a wafer 200 is shown. The wafer may comprise silicon, although other materials may also be used, such as Ge, GaAs, InP, or sapphire (single crystal $Al_2O_3$. In some embodiments, the wafer has the same crystal structure as Ge, with some lattice mis-match, and silicon may be used in those embodiments.

An oxide mask 202 is shown deposited on the wafer 200, with openings 204 therein. The oxide mask 202 may comprise silicon dioxide, thermally grown or deposited by CVD or PECVD. The aspect ratio (ratio of mask thickness to opening width) may be important, typically with a mask thickness of 2 to 4 times the opening width. The mask thickness range may be 200 to 2000 nm, with opening widths of 100 to 500 nm. As an example, the oxide film 202 may be 100 nm thick and the openings 204 may be 50 nm wide. As an alternative to the oxide, a two-layer insulator, such as $SiO_2/Si_3N_4$ may be employed, using one layer as an etch stop for the other layer when etching away a part of the dielectric to form the trapezoid structure on the pedestal, described below. The openings 204 may be formed by various lithography techniques, such as photo, e-beam, or nanoimprint, or self-assembly or by other patterning techniques.

If the wafer 200 comprises Si, then $SiO_2$ is conveniently employed as the oxide mask 202, although other oxides may also be used, such as PECVD silicon oxynitride or amorphous $Al_2O_3$ or low stress silicon nitride (LPCVD).

Selective epitaxy of Ge 206 is seeded from the wafer 200, through the openings 204. For example, CVD with $GeH_4$ precursor in $H_2$ at moderate temperature (~400° C.) may be used to form the Ge 206. The limiting step is cleaning exposed regions of Si so they are clean enough to allow incoming Ge atoms to "see" the underlying Si lattice. That often requires higher temperatures, which can degrade already formed structures. On the other hand, baking at a temperature the same as or less than the subsequent post-epitaxial growth annealing temperature may be sufficient.

The epitaxial growth is continued until lateral overgrowth of the Ge 206 takes place, as shown in FIG. 2B. The initial growth in the trenches 204 is "vertical", i.e., normal to the substrate 200 surface. After the trench 204 is filled to top, growth spreads in any direction that is not constrained by another structure (as well as continuing to grow in the vertical direction).

The ratio of lateral to vertical growth rate is about one for Si and Ge, so it can grow laterally as far as the device can tolerate vertical thickness, which could be many microns (maybe even tens of microns), but smaller dimensions are relevant for field-effect devices, such as disclosed herein. The lateral overgrowth is shown as "buttons" 208 of trapezoidal shape, having "stems", or pedestals, 206.

The assembly is annealed, as described in Step 108 above (FIG. 1), to convert the overgrowth portion 208 into semi-cylindrical vaults 208', as depicted in FIG. 2C.

Generally an insulating layer may need to be formed over the semiconductor layer before the device can be used as field-effect sensor. In an embodiment, an ultra-thin sacrificial layer (not shown) may be next deposited on the vaults. This sacrificial layer may or may not be epitaxially deposited. The sacrificial layer may comprise silicon or silicon-germanium, which is oxidized to form the insulating layer. In another embodiment, the insulator may be formed directly on the Ge. In some embodiments, the functional coating may be able to serve as the insulator.

Figure 3A:
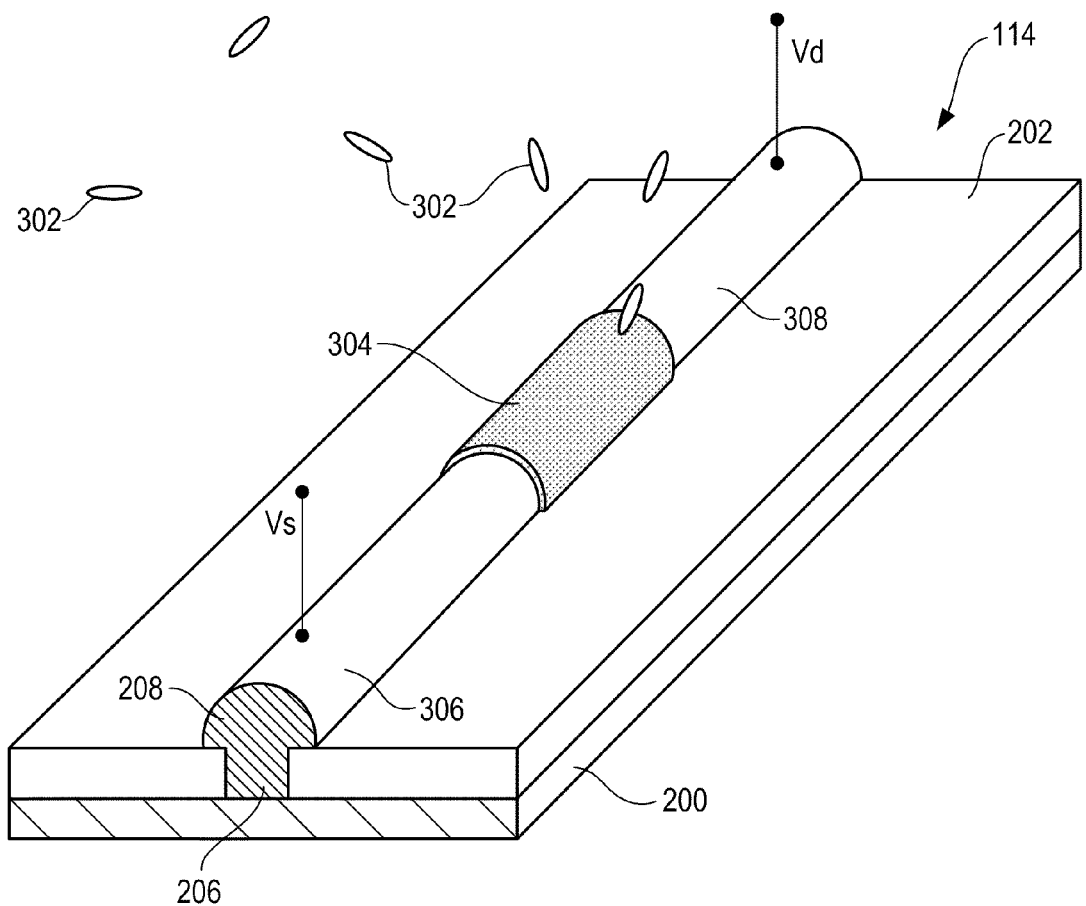
FIGS. 3A-3D are cross-sectional views, depicting a field-effect sensor and a MOSFET, respectively, with vaulted three-dimensional channels (FIGS. 3A and 3B) and a field-effect sensor and a MOSFET, respectively, with omega-shaped three-dimensional channels (FIGS. 3C and 3D), each in accordance with embodiments of the invention.

At this stage, electrodes can be attached to source and drain regions (discussed below) and the device configured as a field-effect sensor. As is conventional, good electrical contact to the source and drain regions may be made by first heavily doping these regions prior to depositing the electrode metal. As indicated above, the surface of the semi-cylindrical vaults may be functionalized (or not), so as to form a sensing surface for molecules, biological species, etc. An embodiment of such a sensor 114 is depicted in FIG. 3A, discussed in greater detail below.

Continuing further in the process for forming MOSFETs, in an embodiment, an ultra-thin epitaxial cap layer 210 may be next deposited on the vaults 208' (the deposition may be epitaxial or not); see FIG. 2D. By "ultra-thin" is meant that the thickness of this layer ranges from about 1 to 5 nm. The cap layer 210 may comprise silicon or silicon-germanium or silicon nitride. In another embodiment, the insulator may be formed directly on the Ge.

Oxidation of the silicon or silicon-germanium cap layer 210 is performed next. Thermal oxidation may be employed. A $SiO_2$ gate oxide 212 is thereby formed. The gate oxide 212 has a thickness that depends on the thickness of cap layer 210. For pure Si, the ratio of oxide thickness to Si consumed is about 2:1. For SiGe, the ratio is somewhat greater. In any event, the thickness of the gate oxide 212 may be in the range of about 2 to 10 nm. The resulting structure is shown in FIG. 2E.

In some embodiments, the preceding two steps may be replaced by deposition of a gate dielectric 212, such as high-κ dielectrics. Examples of such high-κ dielectrics, which have a higher dielectric constant (κ) than silicon dioxide, include $HfO_2$, $ZrO_2$, hafnium silicate, zirconium silicate, silicon nitride, and aluminum oxide. Deposition techniques for such high-K dielectrics are well-known; examples include chemical vapor deposition (CVD), atomic-layer deposition (ALD), and, in some cases, plasma-enhanced CVD (PECVD).

Next, a gate electrode 214 is formed over the gate oxide (or dielectric) 212 and is patterned, producing a gate electrode stack. The resulting structure is depicted in FIG. 2F.

Figure 3B:
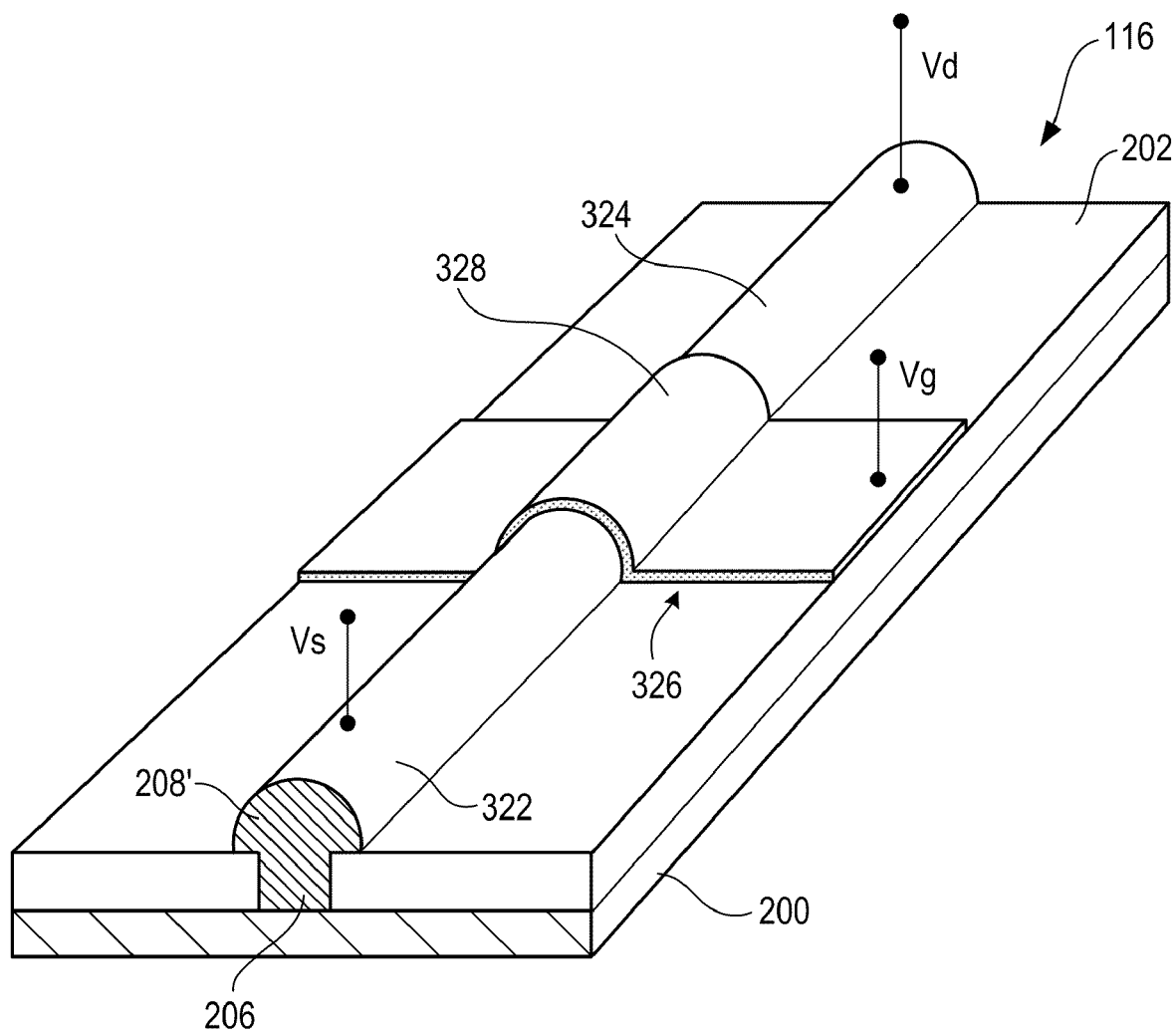

At this stage, electrodes can be attached and the device configured as a MOSFET. As indicated above, contacts are made to source and drain regions and above the gate insulator. As is conventional, good electrical contact to the source and drain regions may be made by first heavily doping these regions prior to depositing the electrode metal. An embodiment of such a MOSFET 116 is depicted in FIG. 3B, discussed in greater detail below.

An alternate process embodiment is depicted in FIGS. 2A-2B and 2G-2I. In this embodiment, omega-shaped 3-D channels are formed.

Figure 2G:
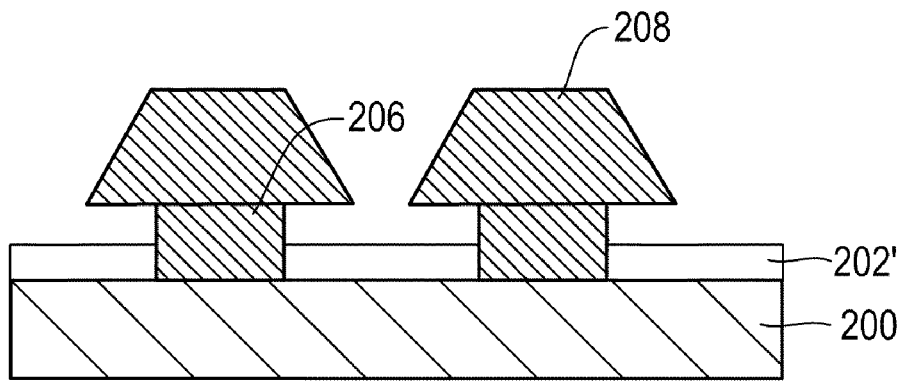

The process sequence in FIGS. 2A-2B is discussed above. Following the lateral overgrowth step in FIG. 2B, a partial etch of the oxide mask layer 202 is performed. An etch-stop mechanism may be employed, such as depositing an etch-stop layer during the deposition of the oxide layer or timing the oxide etch to stop part way through the oxide layer. The resulting structure is depicted in FIG. 2G, showing the reduced thickness of the oxide mask layer 202'.

Figure 2H:
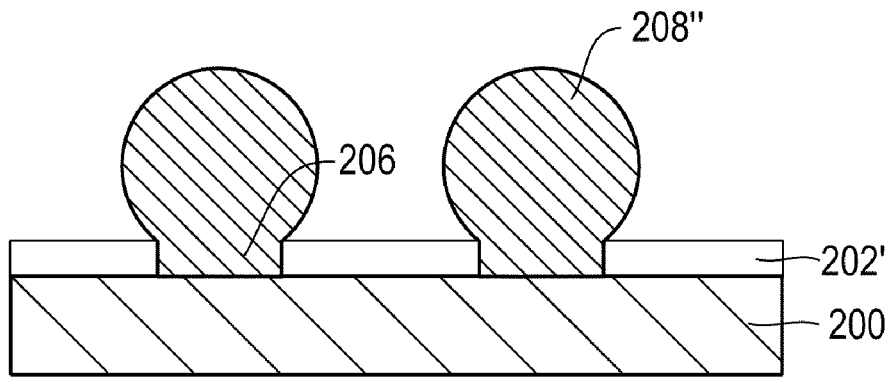
Figure 2I:
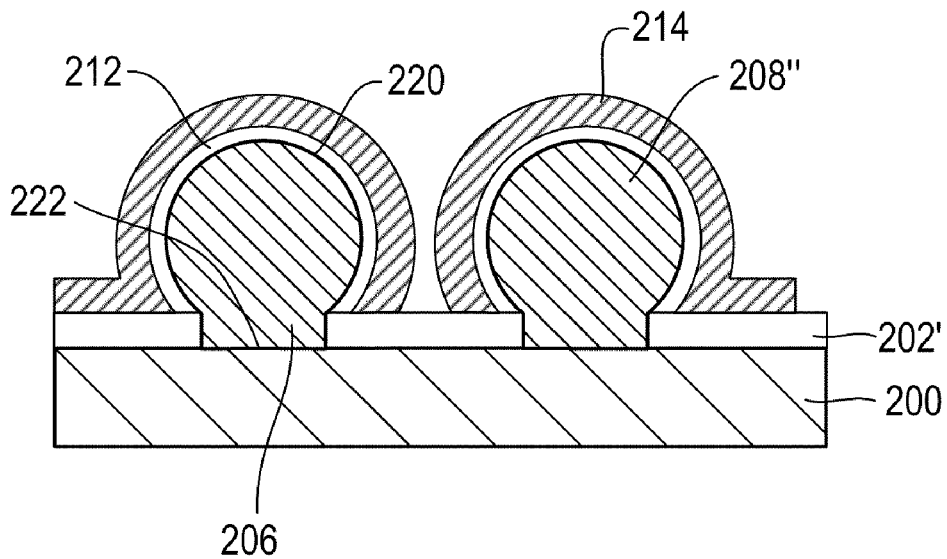

The annealing step (Step 108—FIG. 1) discussed in connection with FIG. 2C is now performed, and the resulting omega-shaped semi-cylindrical channel 208'' shown in FIG. 2H is formed.

As with the vaulted geometry, generally an insulating layer may need to be formed over the semiconductor layer before the device can be used as field-effect sensor. In some cases, the functional coating may be able to serve as insulator.

Figure 3C:
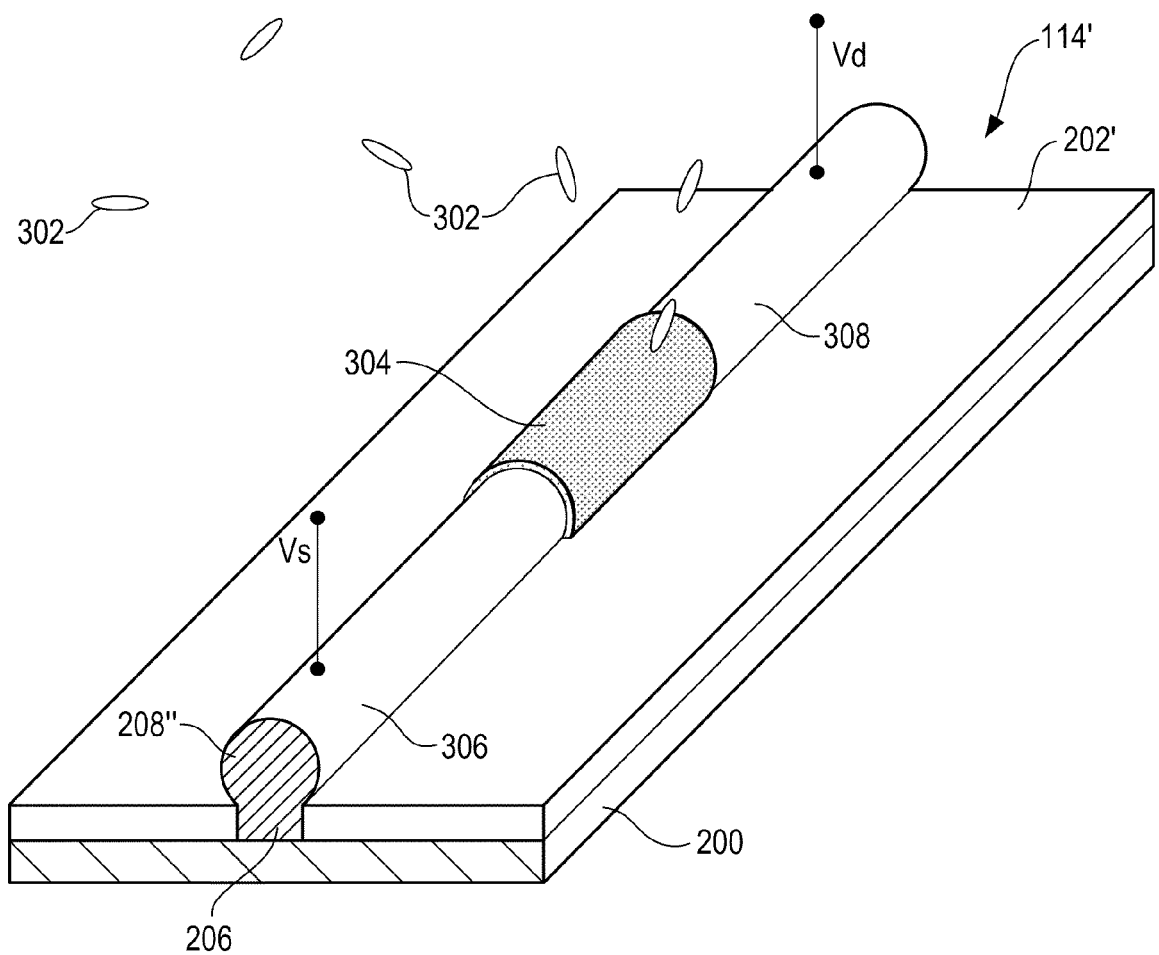

At this stage, electrodes can be attached and the device configured as a field-effect sensor. As indicated above, the surface of the semi-cylindrical channels may be functionalized (or not), so as to form a sensing surface for molecules, biological species, etc. An embodiment of such a sensor 114' is depicted in FIG. 3C, discussed in greater detail below.

Continuing further in the process for forming MOSFETs, the ultra-thin epitaxial cap layer 210 is next deposited on the omega-shaped 3-D channels 208'', as discussed above in connection with the deposition of the cap layer on the vaults 208'. The oxidation (thermal, in some embodiments) of the cap layer 210 is performed to form the gate oxide 212. Alternatively, the high-κ dielectric layer 212 is formed in place of the cap layer 210 and gate oxide 212. In any event, the gate electrode 214 is formed over the gate oxide (or dielectric) 212 and is patterned, producing a gate electrode stack. The resulting structure is depicted in FIG. 2I.

Figure 3D:
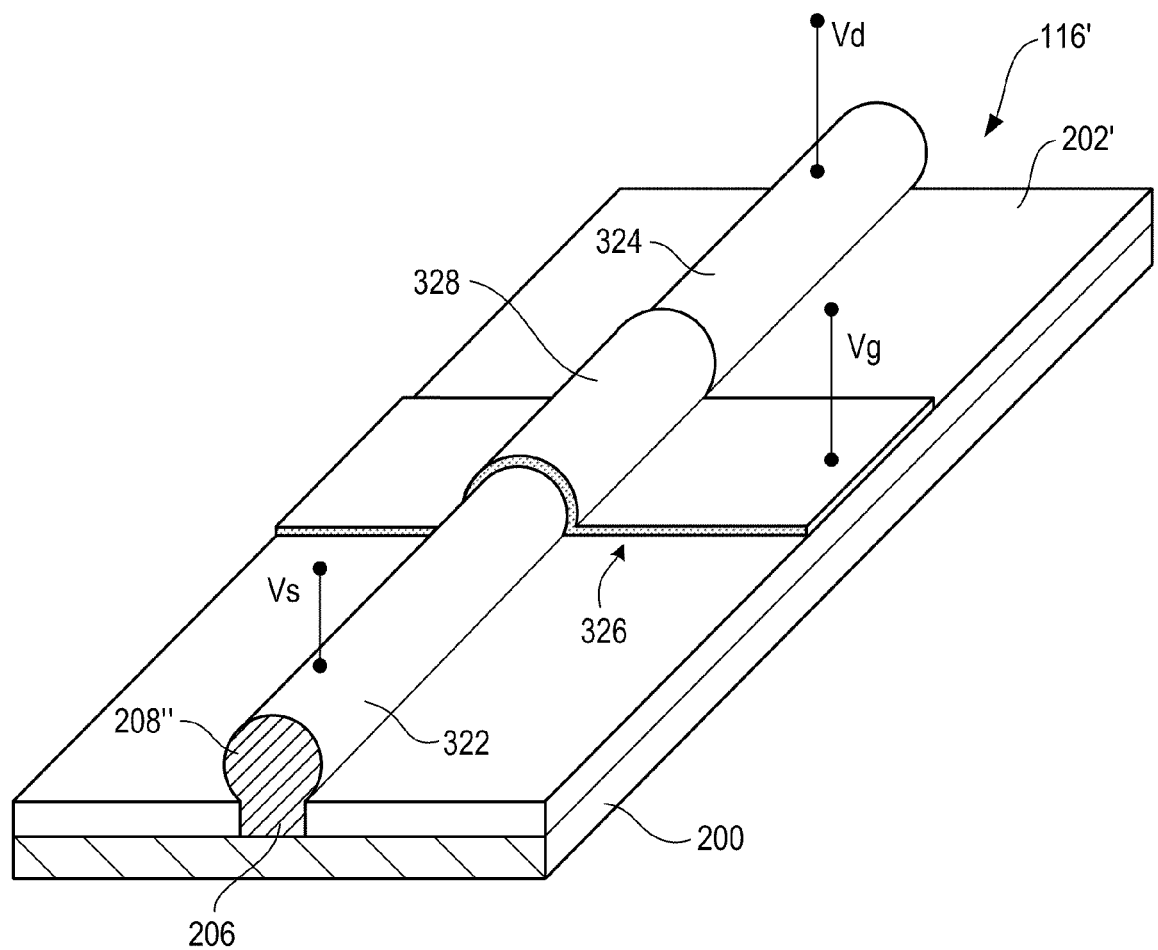

At this stage, electrodes can be attached and the device configured as a MOSFET. As indicated above, contacts are made to source and drain regions and to the gate oxide. An embodiment of such a MOSFET 116' is depicted in FIG. 3D, discussed in greater detail below.

FIG. 3A depicts a Ge-based field-effect sensor 114 with vaulted 3-D channels 208'. The sensor is configured to sense an analyte 302 by means of charge arising from the analyte inducing compensating charge in the channel, which is Ge, through the overlying gate dielectric 304, which may be functionalized (provided with a functionalizing agent for sensing the analyte and shown as stippled). The sensor dielectric 304 may or may not be $SiO_2$ or other oxide. The portion of Ge forming the channel may be doped in some embodiments to adjust the depletion region thickness appropriately.

By suitable doping, source 306 and drain 308 are formed. Examples of suitable dopants include Group V (e.g., phosphorus or arsenic) for forming n-type source and drains and Group III (e.g., boron) for forming p-type source and drains, as is well-known. The dopant concentration is typically greater than $10^{18}$ cm$^{-3}$, and in some embodiments may be greater than $10^{19}$ cm$^{-3}$ or $10^{20}$ cm$^{-3}$. For depletion-mode devices, the dopant type is the same type as the channel. For inversion-mode devices, it is of the opposite type. Electrical connections are made to the source 306 and drain 308 ($V_S$ and $V_D$, respectively).

In operation, voltage is applied to the source 306 and drain 308 and the analyte 302 attaches to or otherwise alters the electronic conductance of the channel (Ge), thus modulating the conductance of the channel 304. The charge on the dielectric or the functional coating may be an intrinsic charge in the molecule or may be generated by an interaction with the functional coating. The charge is most effective if it is closer to the surface of the gate dielectric or functional coating, rather than spaced from it (e.g., by the length of a molecule perpendicular to the surface of the gate dielectric). A positive charge on or near the surface of the dielectric induces a negative charge in the channel, and a negative charge induces a positive charge. An induced negative charge increases the conductance of an n-type channel and decreases the conductance of a p-type channel. For a depletion mode device, the conductance change is caused by a change in the electrically conducting cross-sectional area of the channel by modulating the charge in the depletion region and therefore its thickness. For an accumulation mode device, the number of conducting charge carriers in the channel near its surface is modified.

FIG. 3B depicts a Ge-based MOSFET 116 with vaulted 3-D channels 208'. The MOSFET comprises a source 322, drain 324, and gate electrode 326. The gate electrode 326 is formed between the source 322 and drain 324. A portion 328 of the gate electrode 326 covers the gate dielectric layer (not shown in this drawing). The gate electrode 326 is a highly conducting material, such as metal or highly doped polycrystalline silicon.

The source 322 and drain 324 are formed by suitable doping, employing the same dopants and concentrations described above.

Electrical connections are made to the source 322, gate 326, and drain 324 ($V_S$, $V_G$, and $V_D$, respectively).

FIG. 3C depicts a Ge-based field-effect sensor 114' with omega-shaped 3-D channel 208". The device is the same as depicted in FIG. 3A, but the shape of the 3-D channel 208" is omega-shaped, rather than vaulted.

FIG. 3D depicts a Ge-based MOSFET 116' with omega-shaped 3-D channels 208". The device is the same as depicted in FIG. 3B, but the shape of the 3-D channel 208" is omega-shaped, rather than vaulted.

There are a number of benefits based on electrostatic and materials considerations. For example, on the electrostatic side, in the configurations depicted in FIGS. 2F and 2I, the three-dimensional surrounding of the gate (at least around one-half of its circumference) provides greater electrostatic control over the channel 208', 208". The gate-field is concentrated onto the dielectric-channel interface 220, which means that a thicker dielectric 212 can be used than in conventional devices. Full channel depletion at lower gate voltages becomes possible. The geometry also aids capacitive decoupling of the channel 208' 208" from the substrate 200 by the Ge "stem" 206 results in decreased parasitic capacitance.

On the materials side, the use of an integrated epitaxial Ge channel 208', 208" provides higher mobility than found in Si. The optional thin Si layer over the Ge decreases interface states at the semiconductor-dielectric interface and (in some cases) provides the Si atoms needed to form a thermally-grown silicon dioxide dielectric. The channel itself 208', 208" has almost atomically smooth surface, decreasing surface scattering and increasing carrier mobility and therefore current carrying capability and transconductance of the device. Relatively low processing temperatures are employed, with epitaxial growth of Ge taking place around 400° C. and annealing at about 700° to 900° C.

EXAMPLES

1. Effect of Annealing in Hydrogen on Ge Grown by Selective Heteroepitaxy

Ge grown by selective epitaxy was evaluated with and without high-temperature annealing in hydrogen.

The samples were prepared and processed as follows:

A layer of 1100 Å-thick thermal oxide ($SiO_2$) was grown onto a bare Si wafer. The Si wafer had a (001) orientation.

Photoresist was spin-coated onto the oxide layer and patterned into an etch mask of 2 µm-wide, 2 µm-spaced lines by contact lithography. The lines were oriented parallel to the <110> direction of the substrate.

The oxide exposed through the photoresist mask was etched away using buffered oxide etchant (BOE).

The photoresist was removed, and the sample was dipped in BOE for 3 seconds to remove native oxide.

Ge heteroepitaxy was performed in a chemical-vapor-deposition (CVD) reactor for 25 minutes, after which some samples were annealed in an $H_2$ ambient at 850° C. for 120 minutes.

As used herein, the conventional crystallographic notations are employed. The use of brackets '[ ]' herein in conjunction with such numbers as '111' and '110' pertains to a direction or orientation of a crystal lattice and is intended to include directions '< >' within its scope for simplicity herein. The use of parenthesis '( )' herein with respect to such numbers '111' and '110' pertains to a plane or a planar surface of a crystal lattice and is intended to include planes '{ }' within its scope for simplicity herein.

Figure 4B:
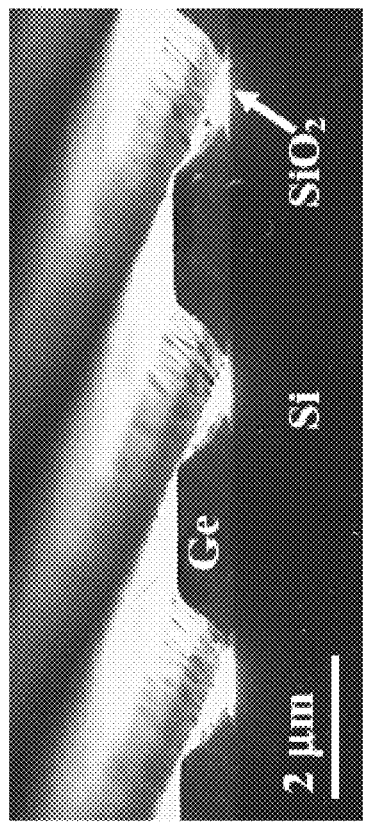
FIGS. 4A-4B are each a perspective view in cross-section of SEM images of Ge selectively grown for 25 minutes only (FIG. 4A) and Ge grown for 25 minutes, then annealed at 850° C. for 120 minutes in a $H_2$ ambient (FIG. 4B) in accordance with an embodiment of the invention; the size bar is approximate.
Figure 4A:
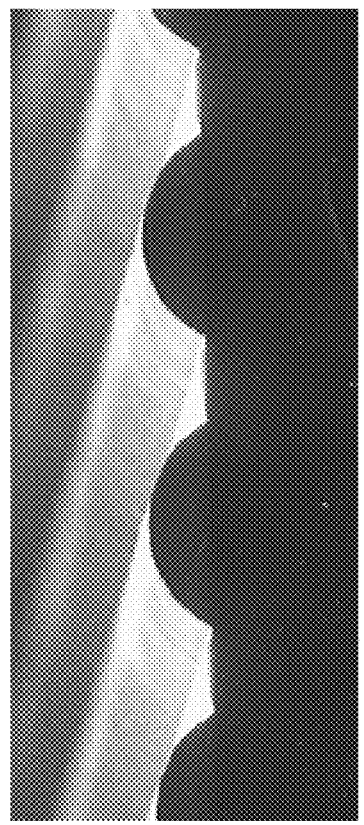

FIG. 4A shows a cross-sectional scanning electron microscope (SEM) image of selectively grown Ge lines without subsequent hydrogen annealing. The image reveals a faceted morphology, with severe roughness visible on the facet walls. The edges of the lines have partially overgrown the adjacent oxide lines. FIG. 4B shows the Ge lines after the 120 minute hydrogen anneal. The most obvious difference is the rounded cross-section of the lines. The roughness of the lines in the lateral direction also has decreased significantly.

2. Effect of Annealing in Hydrogen on Subsequent Epitaxial Growth of Ge

A second layer of epitaxial Ge was grown after the hydrogen anneal step and evaluated. The in-plane orientation of the oxide lines was varied to be parallel to either the <100> or <110> directions of the underlying substrate. Selective Ge growth was first performed for 15 minutes for both types of samples, and identically processed samples with each alignment were subsequently annealed in $H_2$ for 90 minutes, followed by further growth of Ge for 15 minutes.

Figure 5B:
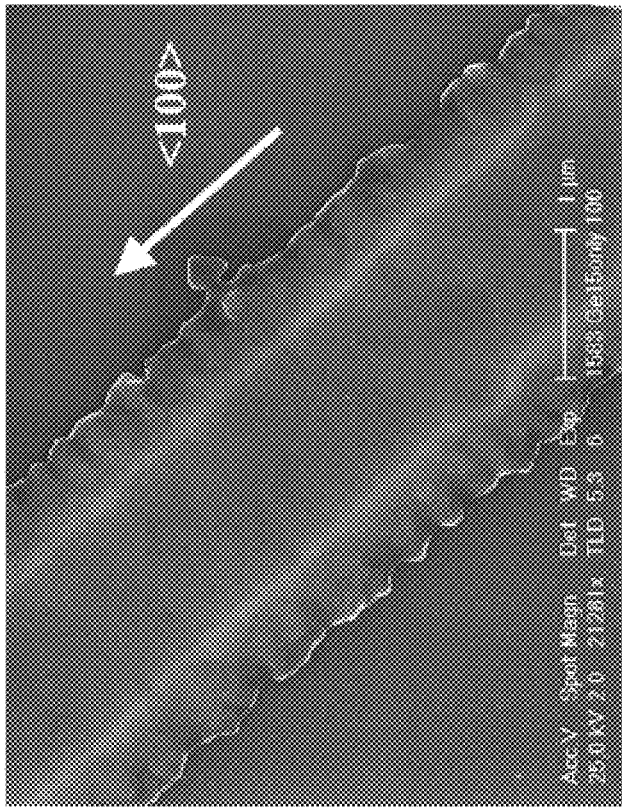
FIGS. 5A-5B are each plan-view SEM images of Ge selectively grown for 15 minutes, which are line oriented in the <110> direction (FIG. 5A) and line oriented in the <100> direction (FIG. 5B) for comparative purposes with the images depicted in FIGS. 6A-6B.
Figure 5A:
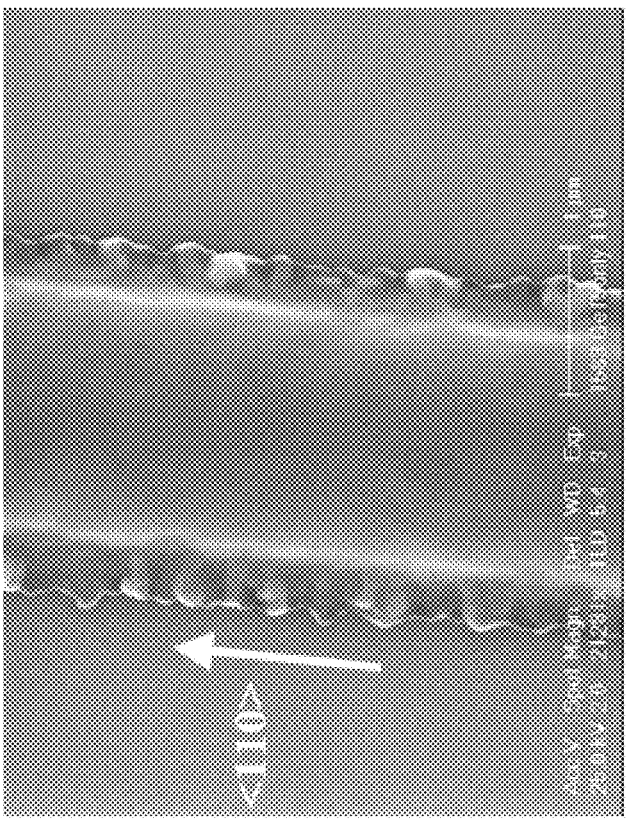

Plan-view SEM images of the selective epitaxial Ge microstructures with no hydrogen annealing are shown in FIGS. 5A-5B. The white arrows indicate the direction of the patterns with respect to the crystallographic directions in the underlying substrate: in FIG. 5A, the line pattern is parallel to the <110> direction, and in FIG. 5B, it is parallel to the <100> direction. The roughness of the laterally extending facets (edges) of the line is clearly observed. Also, faint, faceted, surface features are visible on the top plateau portion of the lines.

FIGS. 6A-6B show the corresponding microstructures after a 90 minute $H_2$ anneal at 850° C. and an additional 15 minutes of Ge growth. Even with the increased cumulative growth time, the roughness at the edges is drastically decreased (FIG. 6A), and eliminated in the case of the lines oriented in the <100> direction (FIG. 6B).

In the foregoing description, numerous details are set forth to provide an understanding of the present invention. However, it will be understood by those skilled in the art that the present invention may be practiced without these details. While the invention has been disclosed with respect to a limited number of embodiments, those skilled in the art will appreciate numerous modifications and variations therefrom. It is intended that the appended claims cover such modifications and variations as fall within the true spirit and scope of the invention.

What is claimed is:

1. A process for fabricating a rounded three-dimensional germanium active channel for transistors and sensors, the process comprising:

providing a crystalline silicon substrate;

forming an insulator mask on the crystalline silicon substrate;

patterning the insulator mask with trenches to expose regions of the silicon substrate;

epitaxially growing germanium selectively in the trenches, seeded from the silicon wafer;

optionally etching the insulator mask partially, so that the cross section of the germanium resembles a trapezoid on a stem; and annealing at least the germanium at an elevated temperature so as to cause the germanium to deform and form the rounded channel.

2. The process of claim 1 wherein the annealing is performed in vacuum, hydrogen, or inert gas ambient.

3. The process of claim 1 further comprising:

doping source and drain regions in the channel to define an un-doped region of the channel therebetween; and forming a gate dielectric over at least the undoped region of the channel and functionalizing a region along the surface in between the source and drain regions with a receptor species or nanostructure that will specifically bind a target molecule or species and be altered in its electronic state, thereby forming a field-effect sensor, wherein a current passing through the channel under a voltage bias from one end to the other is affected by the presence of molecules or species attached to its surface.

4. The process of claim 3 wherein the insulating layer is formed on the channel after the steps of doping and forming and a window is patterned in the insulating layer to selectively expose a portion of a channel surface or a portion of the gate dielectric for functionalization.

5. The process of claim 4 further comprising attaching electrodes to either end of the rounded channel.

6. The process of claim 1 further comprising:

forming and patterning a gate dielectric and gate electrode onto this the rounded channel to form a gate stack of a MOSFET device.

7. The process of claim 6 further comprising patterning the gate electrode and adding dopants into the rounded channel to form source and drain regions located on parts of the germanium cylinder rounded channel on either side of the gate stack; and attaching electrodes to the gate electrode, the source region, and the drain region, thereby forming the MOSFET device.

8. The process of claim 6 wherein the gate dielectric is an oxide formed by growing a thin layer of silicon or silicon-germanium selectively onto the channel surface and oxidizing it.

9. The process of claim 7 wherein metal-semiconductor Schottky junctions are formed at the source and drain regions, with the channel, gate stack, and source and drain regions together defining a germanium MOSFET device.

10. The process of claim 1 wherein the step of epitaxially growing germanium includes further growing germanium until it overgrows the mouth and edges of the trenches and begins to protrude outwards, wherein the epitaxial germanium body outside of the trench mouth has a trapezoidal cross-section.

11. The process of claim 1 wherein in the step of annealing, the elevated temperature is in the range of about 700° to 900° C.

12. The process of claim 1 wherein the rounded channel is vaulted.

13. The process of claim 1 wherein the rounded channel is omega-shaped.

14. The process of claim 1 wherein the insulator mask comprises $SiO_2$.

* * * * *

UNITED STATES PATENT AND TRADEMARK OFFICE
CERTIFICATE OF CORRECTION

PATENT NO. : 8,101,473 B2  Page 1 of 1
APPLICATION NO. : 12/501259
DATED : January 24, 2012
INVENTOR(S) : Hans Cho et al.

It is certified that error appears in the above-identified patent and that said Letters Patent is hereby corrected as shown below:

In column 11, line 33, in Claim 6, after "onto" delete "this".

In column 12, line 4, in Claim 7, after "germanium" delete "cylinder".

Signed and Sealed this
Sixteenth Day of October, 2012

David J. Kappos
*Director of the United States Patent and Trademark Office*